United States Patent [19]

Armstrong et al.

[11] Patent Number: 4,704,086

[45] Date of Patent: Nov. 3, 1987

[54] J-HOOK FORCE-ADJUSTABLE AND DISCONNECTIBLE CONNECTOR FOR ORTHODONTIC HEADGEAR

[75] Inventors: Maclay M. Armstrong, Seattle; Steven A. Houser, Edmonds, both of Wash.

[73] Assignee: Unitek Corporation, Monrovia, Calif.

[21] Appl. No.: 913,871

[22] Filed: Sep. 30, 1986

[51] Int. Cl.$^4$ ............................................. A61C 3/00
[52] U.S. Cl. ........................................................ 433/5
[58] Field of Search ............................................ 433/5

[56] References Cited

U.S. PATENT DOCUMENTS

| | | | |
|---|---|---|---|
| 3,526,035 | 9/1970 | Armstrong | 433/5 |
| 4,368,039 | 1/1983 | Armstrong | 433/5 |
| 4,392,825 | 7/1983 | DeWoskin | 433/5 |
| 4,553,933 | 11/1985 | Armstrong et al. | 433/5 |
| 4,553,934 | 11/1985 | Armstrong et al. | 433/5 |

Primary Examiner—John J. Wilson
Attorney, Agent, or Firm—Robert W. Beach; Ward Brown

[57] ABSTRACT

A force-producing connector connecting a force reaction orthodontic headcap or neckstrap and a J-hook for applying a force to a wearer's jaw includes a slide carrying a force-producing spring and guided for movement lengthwise of an elongated sidepiece base. The elongated base has a row of slots extending lengthwise of it selectively engageable by the toe of a pawl pivoted on the slide, which pawl can be held in locking position by a latch including an aperture in the pawl engageable with a catch on a post carried by the slide over which the pawl aperture can be moved.

14 Claims, 8 Drawing Figures

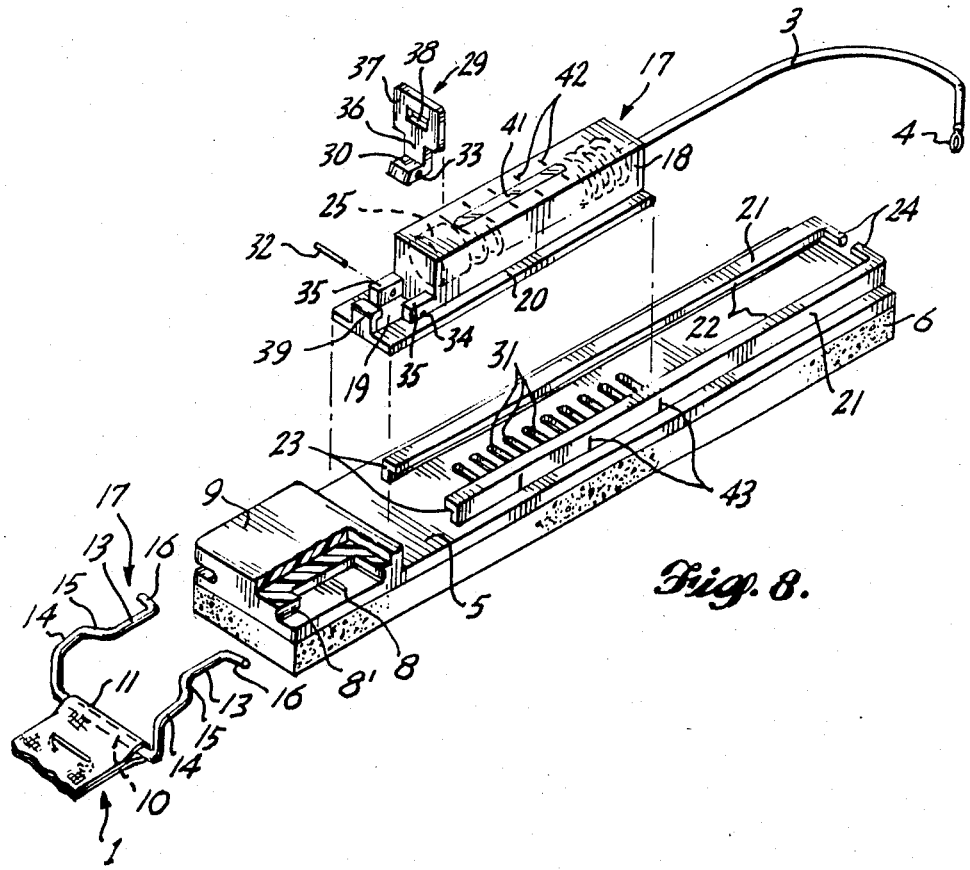

J-HOOK FORCE-ADJUSTABLE AND DISCONNECTIBLE CONNECTOR FOR ORTHODONTIC HEADGEAR

BACKGROUND OF THE INVENTION

1. Field of the Invention

This invention relates to orthodontic headgear of the J-hook type for transmitting extraoral force from such headgear by the J-hook to intraoral orthodontic apparatus, which force can be adjusted to different degrees and which J-hook is disconnectible automatically from the headgear if a force exceeding a predetermined force is exerted on it.

2. Prior Art

The headgear of the present invention is of the general type shown in FIGS. 5 and 6 of Armstrong U.S. Pat. No. 3,526,035, issued Sept. 1, 1970, which headgear is stated at column 5, line 61 to column 6, line 3, to have a wire-coupling member 71 that includes an inwardly curved portion 77 terminating in an eye 78 that can be connected to an intraoral orthodontic appliance. This general type of orthodontic appliance has become known commonly as a "J-hook type" and that terminology is used in the present specification.

Orthodontic headgear of the force-adjustable type and having a connector which is disconnectible automatically if a force exceeding a predetermined force is exerted on it is disclosed in Armstrong et al. U.S. Pat. No. 4,553,933, issued Nov. 19, 1985. In the headgear of that patent, however, a headcap is connected to a facebow by side straps rather than J-hooks being used as in the present invention.

SUMMARY OF THE INVENTION

A principal object of the present invention is to provide a J-hook type of orthodontic headgear constructed to enable the force applied by such headgear to intraoral apparatus to be altered over a considerable range in small increments.

Another object is to provide such a force-adjustable J-hook orthodontic device which is easy to assemble and which can be adjusted readily to exert different orthodontic forces.

It is also an object is to enable the device to be adjusted for altering the orthodontic force whether or not the J-hook is attached to intraoral apparatus.

A particular object is to provide force-adjusting mechanism which can maintain a force adjustment reliably and which force cannot be altered inadvertently or by the application of pulling force on the headgear.

A further object is to provide such adjustable force mechanism which cannot readily be disassembled or tampered with by a user but which can be disassembled readily by a technician.

An additional object is to provide such force-adjustable orthodontic headgear which is rugged and strong while being compact and attractive in appearance.

The foregoing objects can be accomplished by adjusting mechanism located between each J-hook and a headcap or neckstrap and having a slide movable lengthwise along a base strip to different adjusted positions, which slide can be locked relative to the base strip by engaging the toe of a locking lever in a selected one of a row of locking apertures in the base strip and which locking lever can be held by a latch to maintain the locking lever toe in engagement with such selected toe-engageable aperture.

BRIEF DESCRIPTION OF THE DRAWINGS

FIG. 6 is an enlarged cross section taken on line 6—6 of FIG. 4.

FIG. 7 is a top perspective of the sidepiece shown in FIGS. 2 and 3 with its parts in assembled condition, and FIG. 8 is a similar view showing parts of the sidepiece in exploded relationship.

DETAILED DESCRIPTION

Figure 1:
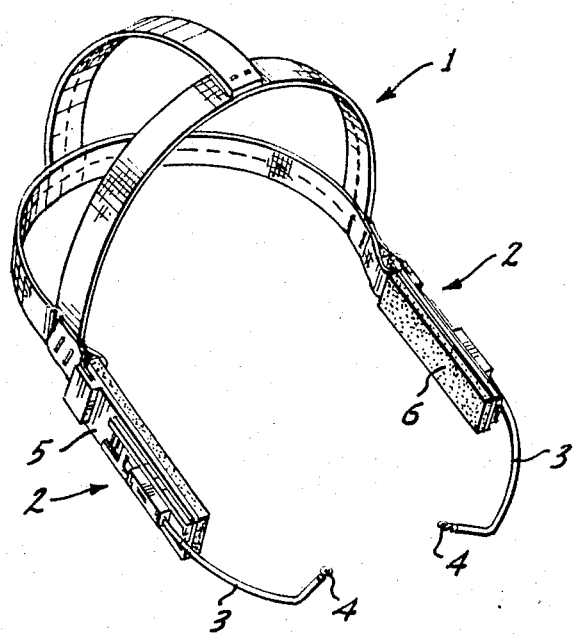
FIG. 1 is a top perspective of a headcap type of J-hook headgear embodying the present invention.

The orthodontic headcap 1 shown in FIG. 1 has opposite sidepieces 2 extending downward and forward from the head-engaging portion of the headcap when the headcap is in place on a wearer's head. Such sidepieces carry J-hooks 3, respectively, having inturned ends terminating in eyes 4 engageable with intraoral orthodontic apparatus. Each sidepiece 2 includes a base strip 5 of hard plastic material such as nylon to the inner side of which is bonded or otherwise attached a foam elastomer liner 6 engageable with a cheek of the wearer.

Figure 3:
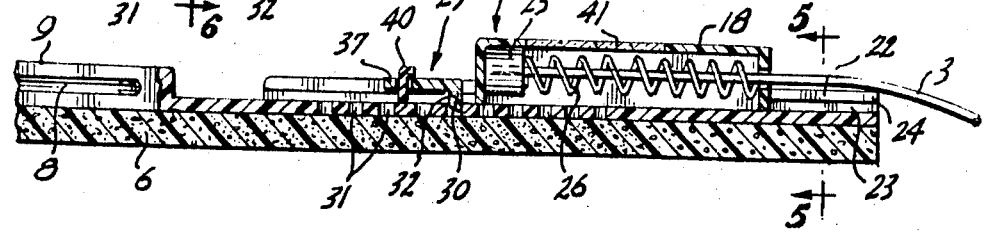
FIG. 3 is a longitudinal section taken on line 3—3 of FIG. 2.

It is important for the sidepieces 2 to be disconnectible from the head-engageable portion of the headcap if a force is exerted on a J-hook in excess of a predetermined force. Consequently, each base strip 5 is connected to the head-engageable portion of the headcap by a disengageable connection generally of the type shown in Armstrong et al. U.S. Pat. No. 4,553,933. The disconnectible connection is composed of a spring clip 7 shown in FIG. 8 having opposite legs clampingly engageable in slots 8 formed in opposite sides of a head 9 integral with and upstanding from the base strip 5, as shown in FIG. 3.

The clip 7 includes a cross member 10 embraced by a fabric loop 11 formed by the forward end portion of the head-engageable portion of the headcap. From opposite ends of the cross member 10 project in parallel relationship offsetting sections 12 carrying inwardly offset clamping portions 13 engageable, respectively, in the opposite slots 8 of the base head 9. Parallel sections 14 and inclined inwardly offsetting sections 15 of the clip join the offsetting portions 12 to the clamping portions 13 of the clip. In assembling the clip 7 onto the head 9 tip portions 16 outturned from the clamping portions 13 of the clip can wedgingly engage the end portions of opposite slots 8 to spread the clamping portions of the clip for insertion endwise into end portions of such slots.

Figure 2:
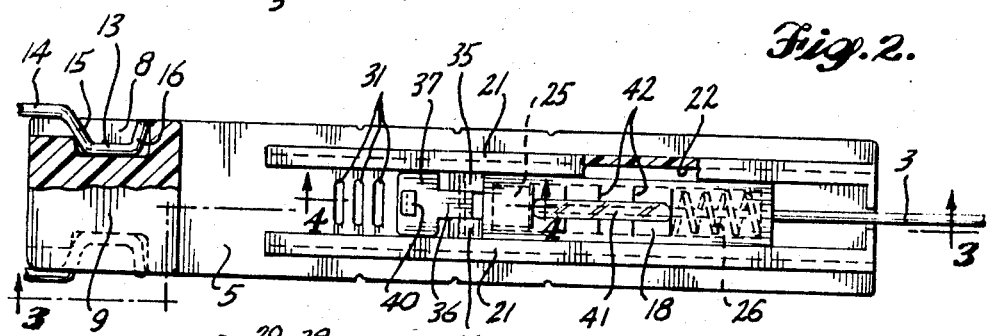
FIG. 2 is a plan of a sidepiece of the headgear shown in FIG. 1.

As shown in FIGS. 2 and 8, each slot 8 has an internal shoulder 8' which may or may not be inclined. Such shoulders are engageable, respectively, by the inclined portions 15 of the spring clips 7 so that a pull on a sidepiece 5 in excess of a predetermined amount will cause the shoulders to wedge the legs 13 of the clip apart to enable the clamping section 13 to slide over the shoulders 8' for release of the clip from the grooves of the sidepiece head 9.

To reconnect the clip 7 with the head 9 on the sidepiece body 5, it is only necessary to enter the outturned end portions 16 of the clip in the ends of the respective grooves 8 and push the clip toward the body until the clamping portions 13 of the clips snap into the grooves 8 beyond the shoulders 8'. The disconnectible connector will thus be restored to its connected condition shown in FIG. 2.

Figure 5:
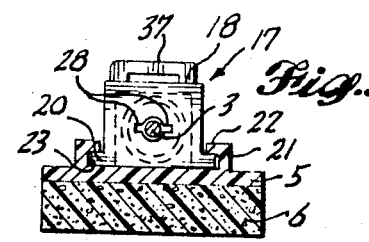
FIG. 5 is a transverse section taken on line 5—5 of FIG. 3.

Adjustment of the orthodontic force is accomplished by shifting the position of slide 17 along the base 5. As shown best in FIGS. 3, 5 and 8, the slide includes a body casing 18 carrying the J-hook 3 and mounted on a bottom plate 19 having edge flanges 20 projecting laterally beyond the opposite sides of the body casing, as shown in FIGS. 5, 6 and 8. Parallel rails 21 of angle cross section are secured in parallel relationship on top of the base 5 disposed so that their upper flanges 22 are inturned in mutually facing relationship, as shown in FIGS. 5, 6, 7 and 8. Such flanges form slots 23 between such flanges and the base for receiving the opposite slide flanges 20, respectively, and guiding them for movement of the slide 17 lengthwise of the base 5.

Movement of the slide 17 relative to the base 5 is limited in one direction by engagement of one slide end with the adjacent side of block 9. Movement of the slide in the opposite direction is limited by engagement of the end of the slide remote from the block 9 with stop fingers 24 shown in FIG. 8 extending toward each other from the corresponding ends of rails 21. The rails may be formed of thermoplastic material so that when heated the fingers 24 can be bent into parallelism with the rails 21, enabling the slide guide flanges 20 to be moved out of the grooves 23 to remove the slide from the base. Initially, the rails can be formed with the stop fingers 24 in outwardly projecting parallel positions and, after the slide has been assembled with the base, the stop fingers can be heated, swung from the broken line positions into the full line stop positions shown in FIG. 8 and then allowed to cool so that the stop fingers will remain in such inturned positions. The customary user will not have sufficient understanding or equipment to bend the fingers 24 into parallel relationship so that the slide can be removed, but this operation can be accomplished easily by a technician with proper equipment. Consequently, the slide and base can be disassembled easily when desired but normally will be kept in assembled relationship.

A knob 25 secured on the end of a J-hook 3 is of a size and shape to be received within the casing 18 of the slide for reciprocation lengthwise of the casing. A helical compression spring 26 through which the shank of the J-hook extends is engaged between the knob 25 and the end wall of the casing nearer the head 9 so that, when a pull is exerted on the J-hook 3 in a direction away from the casing, the shank of the J-hook will be pulled outwardly and draw the knob 25 toward the end of the casing through which the J-hook shank projects to compress the spring 26 and cause it to exert a force on the J-hook.

The J-hook shank extends through the circular central portion of an aperture in the casing end, which aperture has slots 28 extending diametrically oppositely from its central portion. In assemblying the J-hook and the casing 18 initially when the slide is separated from the base 5, the spring 26 can first be threaded onto the J-hook shank over the eye 4 on the J-hook tip and then such tip eye can be moved from the inside of the casing through the aperture slots 28 until one end of the spring 26 engages such casing wall. Movement of the shank through the casing aperture can be continued until the knob 25 can be moved laterally into the open side of the casing. The slide 17 can be assembled with the base by sliding the slide edge flanges 20 into the slots 23 formed by the flanges 22 of rails 21 until the entire base of the slide has passed the fingers 24. These fingers can then be heated and swung from the broken line positions into the solid line positions shown in FIG. 8 and allowed to cool so that such fingers will retain the slide and base in assembled relationship.

When the headcap harness is in place on the head and the eyes 4 of the J-hooks have been secured to intraoral apparatus, the force exerted on such apparatus and the reaction of the headcap harness produced by spring 26 can be adjusted by moving the slide 17 lengthwise of the base 5. Movement of the slide toward the block 9 will increase the orthodontic force produced by spring 26 if J-hook 3 remains stationary. Movement of the slide in the opposite direction relative to the base will progressively decrease such spring force until block 25 bottoms on the casing end remote from the end in which aperture with slots 28 is located.

The slide can be locked in position relative to the base 5 in the position in which the spring 26 is exerting the desired degree of orthodontic force for a given position of the J-hook 3. Such locking of the slide is effected by a locking lever or pawl 29 having a toe 30 engageable in a selected aperture or slot 31 of a row of such apertures extending lengthwise of the base 5, as shown in FIG. 8. The locking lever or pawl is mounted on the slide by a pivot pin 32 extending through a bore 33 in the pawl and having its opposite ends received in apertures 34 in lugs 35 spaced transversely of the slide and projecting upward from its bottom plate 19 at its end nearer the block 9. The neck 36 of the pawl is received between such lugs and carries the head 37 having in its central portion an aperture 38 as shown best in FIGS. 6 and 8.

Figure 4:
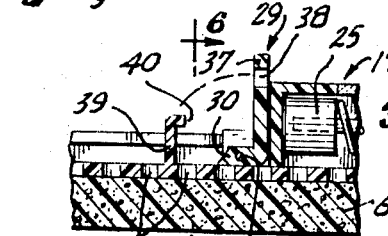
FIG. 4 is a fragmentary enlarged longitudinal section taken on line 4—4 of FIG. 2.

When the head 37 of the locking lever or pawl is swung downward about pin 32, the pawl toe 30 will be swung into a selected one of the base apertures 31 and the head of the pawl will be swung toward the bottom plate 19 of the slide 17. A latch post 39 having a catch lip 40 on its upper end upstands from the bottom plate 19 of the slide in position for passage over it of aperture 38 of the locking pawl head 37 as it is swung toward the bottom plate of the slide as illustrated in FIG. 4. When the locking lever or pawl has been swung toward the slide bottom plate 19 sufficiently so that the aperture 38 passes beyond the catch projection 40, the pawl toe 30 will have engaged in the selected aperture 31 sufficiently to hold the slide reliably fixed in position relative to the base 5 as shown in FIG. 3. With the pawl in that position, a pull on the J-hook 3 will not swing the pawl away from the bottom plate 19 to release the slide.

To free the slide 17 for movement relative to the base 5 into a different position lengthwise of such base, it is merely necessary to raise the head 37 of pawl 29 from the latched position of FIG. 3, releasing catch 40 of the latch post 39, and withdrawing the toe 30 out of the base slot 31 in which it was engaged. When the slide has been shifted to a position such that the locking pawl toe 30 can engage another selected slot 31, the locking lever again is swung down as indicated in FIG. 4 into the latched position of FIG. 3 to lock the slide in the newly adjusted position along base 5. The slots or apertures 31 are located sufficiently close together to enable the force exerted by spring 26 to be adjusted by small increments.

The slide casing 18 has in it an elongated window 41 extending lengthwise of the casing through which the knob 25 on the end of the J-hook shank can be seen. Graduations 42 are arranged on the casing 18 alongside such window, which graduations correspond to degrees of compression of spring 26 that in turn correspond to degrees of force exerted by the spring. Such graduations may, for example, represent forces from 0 ounces to 32 ounces in increments of 8 ounces. The graduations of higher force value will be closer to the end of the casing through which the shank of the J-hook projects.

Also, one or both of the rails 21 may have graduations 43 spaced along its length with which the latch post 39 or an end of the casing 18 can be placed in registration for reference in orthodontic treatment. Thus a particular graduation may correspond to a certain spring force at a particular stage of treatment and correlation of the same slide part with a different graduation at a subsequent stage of treatment and equal spring force will indicate the degree of orthodontic movement accomplished by application of the spring force during the particular treatment period.

We claim:

1. In orthodontic headgear including force reaction means engageable with the head or neck of a wearer, force-applying means for applying force to the wearer's jaw and a force-producing connector connecting the force reaction means, the force-applying means having compression spring means for applying force to the force reaction means and the force-applying means, the improvement residing in the connector comprising a casing housing and receiving pressure from the spring means, an elongated base, cooperating slide-and-guide means interposed between said casing and said elongated base guiding said casing for adjustment in position along said base, and locking means engageable between said casing and said base for holding said casing in a selected position relative to said base.

2. In the orthodontic headgear connector defined in claim 1, the slide-and-guide means including an element having a slot and a flange element engageable in said slot, at least one of said elements being elongated.

3. In the orthodontic headgear connector defined in claim 2, means obstructing the slot to limit movement of the flange element along the slot.

4. In the orthodontic headgear connector defined in claim 3, the slot-obstructing means including a finger of thermoplastic material projecting from the base into the slot, bendable to a position out of the slot upon being heated.

5. In the orthodontic headgear connector defined in claim 1, the locking means including a pawl engageable in a socket.

6. In the orthodontic headgear connector defined in claim 5, the base having a row of sockets elongated parallel to the path of relative movement of the casing and base.

7. In the orthodontic headgear connector defined in claim 6, the locking means including a pawl movable with the casing and engageable selectively with a socket in the base.

8. In the orthodontic headgear connector defined in claim 7, means to hold the pawl in latched socket-engaging position.

9. In the orthodontic headgear connector defined in claim 8, the means for holding the pawl including a catch movable with the casing and engageable with the pawl to hold the pawl in latched position.

10. In the orthodontic headgear connector defined in claim 1, means for indicating a selected position of the casing relative to the base.

11. In the orthodontic headgear connector defined in claim 10, the -and-guide means having cooperating calibrations constituting the means for indicating the selected position of the casing relative to the base.

12. In the orthodontic headgear connector defined in claim 1, means for indicating the position of one end of the spring means relative to the casing.

13. In orthodontic headgear including force reaction means engageable with the head or neck of a wearer, force-applying means for applying force to the wearer's jaw and a force-producing connector connecting the force reaction means and the force-applying means and having spring means for applying force to the force reaction means and the force-applying means, the improvment residing in the connector comprising a slide, an elongated base having guide means guiding said slide for adjustment in position along said base, said base guide means including a slot and said slide having a flange engageable in said slot, slot-obstructing means to limit movement of said flange along said slot including a finger of thermoplastic material projecting from said base into said slot, bendable to a position out of said slot upon being heated, and locking means engageable between said slide and said base for holding said slide in a selected position relative to said base.

14. In orthodontic headgear including force reaction means engageable with the head or neck of a wearer, force-applying means for applying force to the wearer's jaw and a force-producing connector connecting the force reaction means and the force-applying means and having spring means for applying force to the force reaction means and the force-applying means, the improvment residing in the connector comprising a slide, an elongated base having guide means guiding said slide for adjustment in position along said bsse, and locking means including the base having a row of sockets elongated parallel to the path of relative movement of said slide and said base, a pawl engageable selectively with a socket in said base and means to hold said pawl in latched socket-engaging position including a catch carried by said slide and engageable with said pawl to hold said pawl in latched position.

* * * * *

UNITED STATES PATENT AND TRADEMARK OFFICE
CERTIFICATE OF CORRECTION

PATENT NO. : 4,704,086
DATED : November 3, 1987
INVENTOR(S) : Armstrong et al.

It is certified that error appears in the above-identified patent and that said Letters Patent are hereby corrected as shown below:

CLAIM 11: Column 6, line 18, cancel "-and-guide" and insert ...slide-and-guide...

CLAIM 14: Column 6, line 51, cancel "bsse," and insert ...base,...

Signed and Sealed this

Fifteenth Day of March, 1988

Attest:

DONALD J. QUIGG

*Attesting Officer*  *Commissioner of Patents and Trademarks*